United States Patent [19]
Sommer et al.

[11] Patent Number: 5,789,547
[45] Date of Patent: Aug. 4, 1998

[54] METHOD OF PRODUCING INSULIN-LIKE GROWTH FACTOR-I (IGF-I) AND INSULIN-LIKE GROWTH FACTOR BINDING PROTEIN-3 (IGFBP-3) WITH CORRECT FOLDING AND DISULFIDE BONDING

[75] Inventors: Andreas Sommer, Danville; Yasushi Ogawa, Pacifica; Peggy Tao, San Jose, all of Calif.

[73] Assignee: Celtrix Pharmaceuticals, Inc., Santa Clara, Calif.

[21] Appl. No.: 482,271

[22] Filed: Jun. 7, 1995

[51] Int. Cl.$^6$ .............. C07K 1/14; C07K 14/435; C07K 14/65; C12N 15/12

[52] U.S. Cl. .............. 530/351; 530/350; 530/324; 530/344; 530/399; 530/408; 530/412; 435/69.5; 435/172.3

[58] Field of Search .............. 435/69.5, 172.3; 530/399, 412, 408, 324, 344, 350, 351

[56] References Cited

U.S. PATENT DOCUMENTS

| | | | |
|---|---|---|---|
| 4,511,502 | 4/1985 | Builder et al. | 260/112 |
| 4,511,503 | 4/1985 | Olson et al. | 260/112 |
| 4,512,922 | 4/1985 | Jones et al. | 260/112 |
| 4,766,205 | 8/1988 | Ghosh-Dastidar | 530/402 |
| 5,258,287 | 11/1993 | Baxter et al. | 435/69.1 |
| 5,288,931 | 2/1994 | Chang et al. | 530/399 |

FOREIGN PATENT DOCUMENTS

| | | |
|---|---|---|
| 0128733 | 12/1984 | European Pat. Off. |
| WO 91/02807 | 3/1991 | WIPO |
| WO 93/11240 | 6/1993 | WIPO |
| 9319084 | 9/1993 | WIPO |
| WO 93/19084 | 9/1993 | WIPO |
| 95/14034 | 5/1995 | WIPO |

OTHER PUBLICATIONS

Sommer et al., "Molecular genetics and actions of recombinant insulin–like growth factor binding protein–3" *Modern Concepts of Insulin–Like Growth Factors*, Spencer, E.M., ed., (1991) Elsevier, New York. pp. 715–728.

Baxter et al., "Binding proteins for the insulin–like growth factors: structure regulation and function," *Progress in Growth Factor Research*, vol. 1, pp. 49–68, 1989.

Stryer, *Biochemistry*, pp. 32–36 (2d Ed. 1981).

Hober et al., "Folding of insulin–like growth factor I is thermodynamically controlled by insulin–like growth factor binding protein," *Advance ACS Abstracts*, vol. 2, No. 9, May 1, 1994.

Shimasaki et al., "Identification and molecular characterization of insulin–like growth factor binding proteins (IGFBP–1, –2, –3, –4, –5, and –6)," *Progress in Growth Factor Research*, vol. 3, pp. 243–266, 1991.

Hober et al., "Disulfide exchange folding of insulin–like growth factor I," *Biochemistry* 1992, 31, 1749–1756.

Hober et al., "Folding of insulin–like growth factor I is thermodynamically controlled by insulin–like growth factor binding protein," *Biochemistry* 1994, 33, 6758–6761.

Blum et al., "Plasma IGFBP–3 levels as clinical indicators" *Modern Concepts of Insulin–Like Growth Factors* Spencer, E.M., ed., (1991) Elsevier, New York. pp. 381–393.

(List continued on next page.)

*Primary Examiner*—Elizabeth C. Kemmerer
*Assistant Examiner*—David S. Romeo
*Attorney, Agent, or Firm*—Morrison & Foerster LLP

[57] ABSTRACT

The present invention provides a novel method for refolding insulin-like growth factor I (IGF-I) and insulin-like growth factor binding protein 3(IGFBP-3). The method involves mixing of IGF-I and IGFBP-3 together in a cofolding reaction. The inventive cofolding method results in substantially higher yields of correctly folded protein for both molecules and alters the kinetics of refolding. The method includes the production of correctly folded IGF-I, IGFBP-3, and/or IGF-I/IGFBP-3 complex.

34 Claims, 11 Drawing Sheets

OTHER PUBLICATIONS

Rinderknecht et al., "Polypeptides with nonsuppressible insulin–like and cell–growth promoting activities in human serum: Isolation, chemical characterization, and some biological properties of forms I and II" *Proc. Natl. Acad. Sci. USA* (1976) 73:2365–2369.

Baxter et al., "Growth hormone–dependent insulin–like growth factor (IGF) binding protein from human plasma differs from other human IGF binding proteins" *Biochem. Biophys. Res. Comm.* (1986) 139:1256–1261.

Sommer et al., "Molecular genetics and actions of recombinant insulin–like growth factor binding protein–3" *Modern Concepts of Insulin–Like Growth Factors* Spencer, E.M., ed., (1991) Elsevier, New York. pp. 715–728.

Koedam et al., "Insulin–like growth factor (IGFs) and IGF binding protein–3 display disulfide isomerase activity" *Biochem. Biophys. Res. Comm.* (1994) 198:1225–1231.

Williams et al., "Cytoplasmic inclusion bodies in *Escherichia coli* producing biosynthetic human insulin proteins" *Science* (1982) 215:687–689.

Schoner et al., "Isolation and purification of protein granules from *Escherichia coli* cells overproducing bovine growth hormone" *Biotechnol.* (Feb. 1985) pp. 151–154.

Raschdorf et al., "Location of disulphide bonds in human insulin–like growth factors (IGFs) synthesized by recombinant DNA technology" *Biomed. Env. Mass Spectros.* (1988) 16:3–8.

Hober et al., "Folding of insulin–like growth factor I is thermodynamically controlled by insulin–like growth factor binding protein" *Biochem.* (1994) 33:6758–6761.

Sambrook et al., *Molecular Cloning: a Laboratory Manual*, 2nd ed., (1989) Cold Spring Harbor Laboratory Press, New York. (The title page and table of contents are included herewith).

Ausubel et al., eds., *Current Protocols in Molecular Biology* vol. 2, (1987) John Wiley & Sons, New York. (The title page and table of contents are included herewith).

Squires et al., "Production and characterization of human basic fibroblast growth factor from *Escherichia coli*" *J. Biol. Chem.* (1988) 263:16297–16302.

Meacock et al., "Partitioning of bacterial plasmids during cell division: a Cis–acting locus that accomplishes stable plasmid inheritance" *Cell* (1980) 20:529–542.

Liu et al., "Purification of a ubiquitin protein peptidase from yeast with efficient in vitro assays" *J. Bio. Chem.* (1989) 264:20331–20338.

Figure 1

```
1                                                                    50
GPETLCGAEL VDALQFVCGD RGFYFNKPTG YGSSSRRAPQ TGIVDECCFR 51              70
SCDLRRLEMY CAPLKPAKSA
```

Figure 2

```
1                                                                50
ATGCAGATTT TCGTCAAGAC TTTGACCGGT AAAACCATAA CATTGGAAGT 51                                                               100
TGAATCTTCC GATACCATCG ACAACGTTAA GTCGAAAATT CAAGACAAGG 101                                                              150
AAGGTATCCC TCCAGATCAA CAAAGATTGA TCTTTGCCGG TAAGCAGCTA 151                                                              200
GAAGACGGTA GAACGCTGTC TGATTACAAC ATTCAGAAGG AGTCCACCTT 201                                                              250
ACATCTTGTG CTAAGGCTCC GCGGTGGTGG TCCGGAAACC CTGTGCGGTG 251                                                              300
CTGAACTGGT TGACGCTCTG CAGTTCGTTT GCGGTGACCG TGGTTTCTAC 301                                                              350
TTCAACAAAC CGACCGGTTA CGGTTCCTCC TCCCGTCGTG CTCCGCAGAC 351                                                              400
CGGTATCGTT GACGAATGCT GCTTCCGGTC CTGCGACCTG CGTCGTCTGG 401                                        441
AAATGTACTG CGCTCCGCTG AAACCGGCTA AATCCGCTTA A
```

Figure 3

```
1                                                                              50
GASSGGLGPV  VRCEPCDARA  LAQCAPPPAV  CAELVREPGC  GCCLTCALSE 51                                                                            100
GQPCGIYTER  CGSGLRCQPS  PDEARPLQAL  LDGRGLCVNA  SAVSRLRAYL 101                                                                           150
LPAPPAPGNA  SESEEDRSAG  SVESPSVSST  HRVSDPKFHP  LHSKIIIIKK 151                                                                           200
GHAKDSQRYK  VDYESQSTDT  QNFSSESKRE  TEYGPCRREM  EDTLNHLKFL 201                                                                           250
NVLSPRGVHI  PNCDKKGFYK  KKQCRPSKGR  KRGFCWCVDK  YGQPLPGYTT 251           264
KGKEDVHCYS  MQSK
```

Figure 4

```
1                                                              50
GASSAGLGPV  VRCEPCDARA  LAQCAPPPAV  CAELVREPGC  GCCLTCALSE 51                                                            100
GQPCGIYTER  CGSGLRCQPS  PDEARPLQAL  LDGRGLCVNA  SAVSRLRAYL 101                                                           150
LPAPPAPGNA  SESEEDRSAG  SVESPSVSST  HRVSDPKFHP  LHSKIIIIKK 151                                                           200
GHAKDSQRYK  VDYESQSTDT  QNFSSESKRE  TEYGPCRREM  EDTLNHLKFL 201                                                           250
NVLSPRGVHI  PNCDKKGFYK  KKQCRPSKGR  KRGFCWCVDK  YGQPLPGYTT 251           264
KGKEDVHCYS  MQSK
```

Figure 5

```
1                                                              50
ATGGGTGCAT CTTCTGCAGG TTTAGGTCCA GTTGTTCNTT GTGAACCATG 51                                                            100
TGATGCTCGT GCTCTTGCTC AATGTGCTCC ACCACCAGCT GTTTGTGCTG 101                                                           150
AACTTGTTCG TGAACCGGGT TGTGGTTGTT GTCTGACTTG TGCTCTTTCT 151                                                           200
GAAGGTCAAC CATGTGGTAT TTATACTGAA CGTTGTGGTT CTGGTCTGCG 201                                                           250
TTGTCAACCA TCTCCAGATG AAGCTCGTCC TCTGCAGGCT CTGCTGGACG 251                                                           300
GTCGTGGTCT GTGCGTTAAC GCTTCCGCTG TTTCCCGTCT GCGCGCCTAC 301                                                           350
CTGCTGCCAG CGCCGCCAGC TCCAGGAAAT GCTAGTGAGT CGGAGGAAGA 351                                                           400
CCGCAGCGCC GGCAGTGTGG AGAGCCCGTC CGTCTCCAGC ACGCACCGGG 401                                                           450
TGTCTGATCC CAAGTTCCAC CCCTCCATT CAAAGATAAT CATCATCAAG 451                                                           500
AAAGGGCATG CTAAAGACAG CCAGCGCTAC AAAGTTGACT ACGAGTCTCA 501                                                           550
GAGCACAGAT ACCCAGAACT TCTCCTCCGA GTCCAAGCGG GAGACAGAAT 551                                                           600
ATGGTCCCTG CCGTAGAGAA ATGGAAGACA CACTGAATCA CCTGAAGTTC 601                                                           650
CTCAATGTGC TGAGTCCCAG GGGTGTACAC ATTCCCAACT GTGACAAGAA 651                                                           700
GGGATTTTAT AAGAAAAAGC AGTGTCGCCC TTCCAAAGGC AGGAAGGGGG 701                                                           750
GCTTCTGCTG GTGTGTGGAT AAGTATGGGC AGCCTCTCCC AGGCTACACC 751                                                           798
ACCAAGGGGA AGGAGGACGT GCACTGCTAC AGCATGCAGA GCAAGTAG
```

Figure 6

```
1                                                                    50
GGTGCTTCTT CTGCTGGTCT TGGACCAGTT GTTCGTTGTG AACCATGTGA
51                                                                  100
TGCACGAGCT TTAGCTCAAT GTGCTCCACC ACCAGCTGTT TGTGCTGAAT
101                                                                 150
TAGTTCGAGA ACCAGGTTGT GGTTGTTGTT TAACTTGTGC TTTATCTGAA
151                                                                 200
GGTCAACCAT GTGGTATTTA TACTGAACGT TGCGGTAGTG GTTTGCGTTG
201                                                                 250
TCAACCAAGC CCAGATGAAG CTAGGCCTTT ACAAGCATTA TTAGATGGTC
251                                                                 300
GAGGTCTGTG TGTTAATGCG TCCGCTGTTT CTCGATTGCG CGCTTATTTA
301                                                                 350
TTACCTGCCC CACCGGCACC GGGTAACGCC TCCGAAAGCG AAGAGGATCG
351                                                                 400
TTCTGCGGGT TCCGTTGAAT CTCCAAGTGT GAGTTCTACC CATCGAGTTA
401                                                                 450
GCGACCCGAA ATTTCATCCG TTGCACTCTA AAATCATTAT TATTAAAAAG
451                                                                 500
GGTCACGCAA AGGATTCTCA ACGTTATAAG GTGGATTATG AAAGCCAATC
501                                                                 550
TACCGACACT CAAAATTTTA GTAGTGAAAG TAAACGTGAA ACCGAGTACG
551                                                                 600
GCCCGTGTCG ACGTGAGATG GAGGATACCT TAAACCATTT AAAATTTTTG
601                                                                 650
AACGTTTTAT CCCCGCGTGG CGTTCATATC CCGAATTGCG ATAAAAAGG
651                                                                 700
CTTCTACAAA AAGAAACAAT GCCGTCCGAG TAAGGGTCGT AAACGAGGTT
701                                                                 750
TTTGTTGGTG CGTTGACAAA TACGGTCAAC CGTTGCCGGG TTATACTACT
751                                                                 800
AAAGGCAAAG AAGATGTTCA TTGTTATTCT ATGCAATCTA AATAATGCAT
801        811
CTCGAGAATT C
```

Figure 7A

```
1                                                                       50
ATGCAGCGGG  CGCGACCCAC  GCTCTGGGCC  GCTGCGCTGA  CTCTGCTGGT 51                                                                     100
GCTGCTCCGC  GGGCCGCCGG  TGGCGCGGGC  TGGCGCGAGC  TCGGCGGGCT 101                                                                    150
TGGGTCCCGT  GGTGCGCTGC  GAGCCGTGCG  ACGCGCGTGC  ACTGGCCCAG 151                                                                    200
TGCGCGCCTC  CGCCCGCCGT  GTGCGCGGAG  CTGGTGCGCG  AGCCGGGCTG 201                                                                    250
CGGCTGCTGC  CTGACGTGCG  CACTGAGCGA  GGGCCAGCCG  TGCGGCATCT 251                                                                    300
ACACCGAGCG  CTGTGGCTCC  GGCCTTCGCT  GCCAGCCGTC  GCCCGACGAG 301                                                                    350
GCGCGACCGC  TGCAGGCGCT  GCTGGACGGC  CGCGGGCTCT  GCGTCAACGC 351                                                                    400
TAGTGCCGTC  AGCCGCCTGC  GCGCCTACCT  GCTGCCAGCG  CCGCCAGCTC 401                                                                    450
CAGGAAATGC  TAGTGAGTCG  GAGGAAGACC  GCAGCGCCGG  CAGTGTGGAG 451                                                                    500
AGCCCGTCCG  TCTCCAGCAC  GCACCGGGTG  TCTGATCCCA  AGTTCCACCC 501                                                                    550
CCTCCATTCA  AAGATAATCA  TCATCAAGAA  AGGGCATGCT  AAAGACAGCC 551                                                                    600
AGCGCTACAA  AGTTGACTAC  GAGTCTCAGA  GCACAGATAC  CCAGAACTTC 601                                                                    650
TCCTCCGAGT  CCAAGCGGGA  GACAGAATAT  GGTCCCTGCC  GTAGAGAAAT 651                                                                    700
GGAAGACACA  CTGAATCACC  TGAAGTTCCT  CAATGTGCTG  AGTCCCAGGG 701                                                                    750
GTGTACACAT  TCCCAACTGT  GACAAGAAGG  GATTTTATAA  GAAAAAGCAG 751                                                                    800
TGTCGCCCTT  CCAAAGGCAG  GAAGCGGGGC  TTCTGCTGGT  GTGTGGATAA
```

Figure 7B

```
801                                                               850
GTATGGGCAG CCTCTCCCAG GCTACACCAC CAAGGGGAAG GAGGACGTGC 851                  876
ACTGCTACAG CATGCAGAGC AAGTAG
```

Figure 8

```
1                                                                50
ATGAGCGGAG  AAAATCGTGC  TGTGGTGCCG  ATTGAATCAA  ACCCTGAAGT 51                                                              100
TTTTACAAAT  TTTGCACATA  AATTAGGTTT  AAAAAATGAA  TGGGCGTATT 101                                                             150
TCGATATCTA  TAGCTTAACA  GAGCCAGAGT  TACTAGCATT  CTTACCAAGG 151                                                             200
CCAGTGAAGG  CCATTGTGCT  GCTATTTCCG  ATAAACGAGG  ATAGAAAATC 201                                                             250
GAGTACCAGT  CAACAAATTA  CAAGTTCTTA  TGATGTTATA  TGGTTTAAGC 251                                                             300
AATCAGTCAA  AAATGCGTGC  GGATTGTATG  CAATTCTTCA  TTCTTTGAGC 301                                                             350
AATAACCAGT  CATTGTTGGA  GCCCGGCTCC  GACTTGGACA  ATTTTTTAAA 351                                                             400
ATCTCAAAGT  GATACTTCAA  GCTCGAAGAA  TAGGTTTGAT  GATGTTACTA 401                                                             450
CCGACCAATT  CGTCTTGAAT  GTAATAAAAG  AGAATGTACA  AACATTTTCT 451                                                             500
ACTGGCCAGT  CAGAAGCACC  AGAAGCAACT  GCAGATACTA  ATCTACACTA 501                                                             550
TATCACATAT  GTGGAAGAGA  ACGGAGGGAT  ATTTGAACTG  GATGGAAGGA 551                                                             600
ATTTGAGCGG  ACCCTCTAT  TTGGGAAAGA  GTGACCCAAC  TGCCACCGAT 601                                                             650
TTGATTGAAC  AGGAATTAGT  TAGAGTGAGA  GTCGCCTCAT  ATATGGAAAA 651                                                             700
TGCAAATGAA  GAAGATGTAT  TAAACTTTGC  TATGCTAGGA  TTGGGCCCTA 701         711
ATTGGGAATA  A
```

METHOD OF PRODUCING INSULIN-LIKE GROWTH FACTOR-I (IGF-I) AND INSULIN-LIKE GROWTH FACTOR BINDING PROTEIN-3 (IGFBP-3) WITH CORRECT FOLDING AND DISULFIDE BONDING

FIELD OF THE INVENTION

The invention relates generally to the field of production of active, properly folded proteins and particularly to the refolding of insulin-like growth factor-I (IGF-I) and insulin-like growth factor binding protein-3 (IGFBP-3) polypeptides.

BACKGROUND

Growth factors are polypeptides which stimulate a wide variety of biological responses (e.g. DNA synthesis, cell division, expression of specific genes, etc.) in a defined population of target cells. A variety of growth factors have been identified, including transforming growth factor $\beta 1$ (TGF-$\beta 1$), TGF-$\beta 2$, TGF-$\beta 3$, TGF-$\beta 4$, TGF-$\beta 5$, epidermal growth factor (EGF), platelet-derived growth factor (PDGF), fibroblast growth factor (FGF), insulin-like growth factor-I (IGF-I) and IGF-II.

IGF-I and IGF-II are related in amino acid sequence and structure, with each polypeptide having a molecular weight of approximately 7.5 kilodaltons (Kd). IGF-I mediates the major effects of growth hormone, and thus is the primary mediator of growth after birth. IGF-I has also been implicated in the actions of various other growth factors, since treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division) for the cells in neural tissue, muscle, reproductive tissue, skeletal tissue and a wide variety of other tissues.

Unlike most growth factors, the IGFs are present in substantial quantity in the circulation, but only a very small fraction of this IGF is free in the circulation or in other body fluids. Most circulating IGF is bound to IGF-binding protein-3 (IGFBP-3). IGF-I may be measured in serum to diagnose abnormal growth-related conditions, e.g., pituitary gigantism, acromegaly, dwarfism and various growth hormone deficiencies. Although IGF-I is produced in many tissues, most circulating IGF-I is believed to be synthesized in the liver.

Almost all IGF circulates in a non-covalently associated ternary complex composed of IGF-I or IGF-II, IGFBP-3, and a larger protein subunit termed the acid labile subunit (ALS). This ternary complex is composed of equimolar amounts of each of the three components. ALS has no direct IGF-binding activity and appears to bind only to the IGF/IGFBP-3 binary complex. The ternary complex of IGF+IGFBP-3+ALS has a molecular weight of approximately 150 Kd. This ternary complex is thought to function in the circulation "as a reservoir and a buffer for IGF-I and IGF-II preventing rapid changes in the concentration of free IGF" (Blum et al. (1991) "Plasma IGFBP-3 Levels as Clinical Indicators" in MODERN CONCEPTS IN INSULIN-LIKE GROWTH FACTORS, pp. 381–393, (E. M. Spencer, ed., Elsevier, N.Y.).

Most circulating IGF-I, IGF-II and IGFBP-3 is in the form of a complex, accordingly, very little free IGF is detectable. Moreover, a high level of free IGF in blood is undesirable. High blood levels of free IGF lead to serious hypoglycemia due to the insulin-like activities of IGF. In contrast to the IGFs and IGFBP-3, there is a substantial pool of free ALS in plasma which assures that any IGF/IGFBP-3 complex entering the circulation immediately forms a ternary complex.

While IGFBP-3 is the most abundant IGF binding protein in the circulation, at least five other distinct IGF binding proteins (IGFBPs) have been identified in various tissues and body fluids. Although these proteins bind IGFs, they each originate from separate genes and have distinct amino acid sequences. Thus, the binding proteins are not merely analogs or derivatives of a common precursor. Unlike IGFBP-3, other circulating IGFBPs are not saturated with IGFs. None of the IGFBPs other than IGFBP-3 can form the 150 Kd ternary complex.

IGF-I and IGFBP-3 may be purified from natural sources or produced by recombinant means. For instance, purification of IGF-I from human serum is well known to the art (Rinderknecht et al., (1976) *Proc. Natl. Acad. Sci.* (USA) 73:2365–2369). Production of IGF-I by recombinant processes is shown in EP 0.128,733, published in December of 1984. IGFBP-3 may be purified from natural sources using a process such as that shown in Baxter et al. ((1986) "Growth Hormone-Dependent Insulin-Like Growth Factors (IGF) Binding Protein from Human Plasma Differs from Other Human IGF Binding Proteins," *Biochem. Biophys. Res. Comm.* 139:1256–1261). IGFBP-3 may be synthesized by recombinant organisms as discussed in Sommer et al. (supra, pp. 715–728). Recombinant IGFBP-3 binds IGF-I in a 1:1 molar ratio.

Topical administration of IGF-I/IGFBP-3 complex to rat and pig wounds is significantly more effective than administration of IGF-I alone (Sommer et al., supra). Subcutaneous administration of IGF-I/IGFBP-3 complex to hypophysectomized, ovariectomized, and normal rats, as well as intravenous administration to cynomologous monkeys, substantially prevents the hypoglycemic effects of IGF-I administered alone.

Both IGF-I and IGFBP-3 have disulfide isomerase activity when measured individually. However, mixture of the two proteins substantially inhibits this activity (Koedam and Leo van den Brande (1994) "Insulin-Like Growth Factors (IGFs) and IGF Binding Protein-3 Display Disulfide Isomerase Activity" *Biochem. Biophys. Res. Comm.* 198:1225–1231).

Genetic engineering has made it possible to produce large amounts of polypeptides encoded by cloned DNA by means of recombinant expression systems, especially by expression in prokaryotes such as *Escherichia coli*. The expressed heterologous peptide, which would otherwise either not be produced at all by the host cell or be produced only in limited amounts, may constitute a significant proportion of the total cellular polypeptide of the host cell.

Several problems are frequently encountered when cloned DNAs are expressed at high levels in recombinant expression systems. Polypeptides which are overexpressed in the cytoplasm of host cells often accumulate as insoluble "inclusion bodies" or "refractile bodies," particularly when bacteria are utilized as host cells (Williams et al. (1982) *Science* 215:687–688; Schoner et al. (1985) *Biotechnology* 3:151–154) . However, inclusion body formation is not limited to bacterial expression systems. For example, the Krüppel gene product of Drosophila can form inclusion bodies when produced in insect cells using a baculovirus expression system. Polypeptides accumulated in the form of inclusion bodies or refractile bodies are relatively useless for biological and biochemical assays. Conversion of this insoluble material into active, soluble polypeptide requires slow and difficult solubilization and refolding protocols which increase the cost of production of the polypeptide and often greatly reduce the net yield of biologically active polypeptide.

Even when heterologous polypeptides are expressed in the cytoplasm of host cells in soluble form, they may not be biologically active, due to incorrect folding. Incorrect folding may occur in the cytoplasm of host cells or during the isolation procedure.

The difficulty inherent in obtaining biologically active recombinant proteins from recombinant expression systems is increased with polypeptides which contain cysteine residues, such as IGF-I. IGF-I contains six cysteine residues, all of which form intramolecular disulfide bonds which are believed to stabilize the active conformation of the protein. The cysteine residues in IGF-I can form incorrect disulfide bonds, i.e., disulfide bonds formed between cysteine residues not found in native IGF-I. IGF-I molecules containing incorrect disulfide bonds have reduced biological activity (Raschdorf, et al. (1988) Biomed. Env. Mass Spectros. 16:3–8).

It has been found that the amount of soluble polypeptide can be increased in E. coli recombinant expression if the fermentation temperature is lowered below 30° Celsius (C). This procedure is useful as an alternative to renaturation of polypeptides from inclusion bodies but requires an expression system which operates efficiently below 30° C. This procedure may not be commercially feasible, however, since reduction of the fermentation temperature increases the duration and, therefore, the cost of the fermentation with a concomitant increase in the risk of contamination of the culture.

There are many methods of refolding proteins known to the art. For example, U.S. Pat. Nos. 4,511,502, 4,511,503, and 4,512,922 describe methods that are regarded as being universally applicable, with only minor modifications, to the refolding of proteins recovered from inclusion bodies. These methods generally seek to disrupt the structure of improperly folded proteins, then allow weak intramolecular forces, i.e., hydrogen bonding, hydrophobic interactions, and ionic bonding, to fold the protein into its proper conformation, followed by oxidation to form correct disulfide bonds.

In one such method, the protein to be refolded is purified under conditions which maintain the cysteine moieties of the protein as free sulfhydryl groups by the inclusion of a reducing agent throughout the purification process. This allows the protein to refold during the purification process in the absence of incorrect intramolecular disulfide bonds. The reducing agent is then diluted to enable the refolded protein to form disulfide bonds in the presence of air or some other oxidizing agent. This method can be easily incorporated into most purification processes and works optimally for recombinant proteins having relatively uncomplicated tertiary structures.

Another approach is to refold the protein in the presence of both the reduced (R-SH) and oxidized (R-S-S-R) forms of a sulfhydryl compound. This allows disulfide bonds to form, break, and reform throughout the purification process. The reduced and oxidized forms of the sulfhydryl compound are provided in a buffer having sufficient denaturing power that all of the intermediate conformations of the protein remain soluble during the refolding process. Urea is suggested as a suitable denaturant because of its intermediate denaturing power which allows a protein to attain its correct conformation and yet also maintain the solubility of folding intermediates. This approach is most effective when the protein to be refolded has a relatively uncomplicated folding pattern.

An alternative approach which may be used for more difficult refolding situations is to break any disulfide bonds that may have formed during the synthesis or isolation of the protein, then derivatize the free sulfhydryl groups of the protein. Free sulfhydryls are derivatized by sulfonation, which blocks the formation of disulfide bonds. The protein is then refolded in a weak denaturant, then desulfonated, which allows correct disulfide bond formation. Desulfonation takes place in the presence of a sulfhydryl compound. A small amount of the compound's corresponding oxidized form will ensure that suitable disulfide bonds remain intact. The pH is altered, i.e., increased, to a value such that the sulfhydryl compound is at least partially ionized, enhancing the nucleophilic displacement of the sulfonate.

These refolding methods, while practical for their universal applicability, have not been shown to be particularly efficient with IGF-I and may be difficult or burdensome to perform.

Refolding methods have been disclosed which are specific to IGF-I. PCT publications WO 91/02807, WO 93/11240, and WO 93/19084 each disclose methods for refolding recombinantly expressed IGF-I protein.

WO 91/02807 discloses IGF-I fusion proteins, wherein a positively-charged amino acid sequence is fused to the amino-terminus of IGF-I. The amino-terminal addition aids in refolding, such that yields of approximately 50% correctly folded protein are achieved. This approach requires the extra steps of cleavage of the amino-terminal fusion peptide and purification to yield native IGF-I.

WO 93/11240 discloses a method for refolding IGF-I protein in a single solution containing a chaotropic agent, an organic solvent, and a reducing agent at alkaline pH, such that as much as 85% of correctly folded protein is achieved.

WO 93/19084 discloses a method for refolding recombinantly produced IGF-I utilizing a three step refolding protocol. Improperly folded met-IGF-I, i.e., IGF-I with an amino-terminal methionine (this methionine residue must be removed to yield mature IGF-I), is solubilized in a denaturing solution. An oxidizing agent is then added to form a "redox" solution. An additional reducing agent is added to increase disulfide exchange and the solution is incubated overnight. This method results in yields of up to about 30% correctly folded protein. This protein must be further processed to remove the amino-terminal methionine residue.

Recently, Hober et al. ((1994) "Folding of Insulin-Like Growth Factor is Thermodynamically Controlled by Insulin-Like Growth Factor Binding Protein" Biochemistry 33:6758–6761) described a method for refolding IGF-I utilizing the addition of native IGFBP-1. Addition of native IGFBP-1 to reduced IGF-I polypeptide under redox conditions resulted in yields of native IGF-I of up to 89%. Use of IGFBP-3 was not disclosed, nor was the use of unfolded IGFBPs.

The refolding methods known to the art all result in yields of correctly folded protein significantly less than 100%. The heterologous mixture resulting from these methods must then be further purified, a process that can be time consuming and/or costly.

There is a need in the art for a simple, rapid, highly efficient method for refolding IGF and IGFBP-3 into the correct conformation with correct disulfide bonding.

Accordingly, it is an object of the present invention to provide a rapid, highly efficient method for refolding IGF-I and IGFBP-3 by cofolding the two polypeptides, resulting in high yields of properly folded proteins. It is a further object of the present invention to provide a simple, highly efficient method for the production of purified complexes of native IGF and IGFBP-3.

The patents, patent applications and publications cited throughout the disclosure are incorporated herein by reference in their entirety.

BRIEF SUMMARY OF THE INVENTION

In one aspect the invention provides a rapid, highly efficient method for refolding IGF-I and IGFBP-3, and further provides an efficient method for obtaining native IGF-I/IGFBP-3 complexes. The invention further provides for the purification of native IGF-I and native IGFBP-3 from the native IGF-I/IGFBP-3 complexes.

In another aspect the invention provides a rapid, highly efficient method for refolding IGF-I, resulting in very high yields of native IGF-I.

In yet another aspect, the invention provides a rapid, highly efficient method for refolding IGFBP-3, resulting in increased yields of native IGFBP-3.

BRIEF DESCRIPTION OF THE DRAWINGS

FIG. 1 (SEQ ID NO: 1) shows the amino acid sequence of human IGF-I.

FIG. 2 (SEQ ID NO: 2) shows a nucleotide sequence coding for human IGF-I.

FIG. 3 (SEQ ID NO: 3) and FIG. 4 (SEQ ID NO: 4) show two alternate amino acid sequences for IGFBP-3.

FIGS. 5 (SEQ ID NO: 5), 6 (SEQ ID NO: 6), and 7 (SEQ ID NO: 7) show three alternative nucleotide sequences coding for human IGFBP-3.

FIG. 8 (SEQ ID NO: 8) shows a nucleotide sequence coding for yeast ubiquitin hydrolase (YUH).

DISCLOSURE OF THE INVENTION

Figure 9:
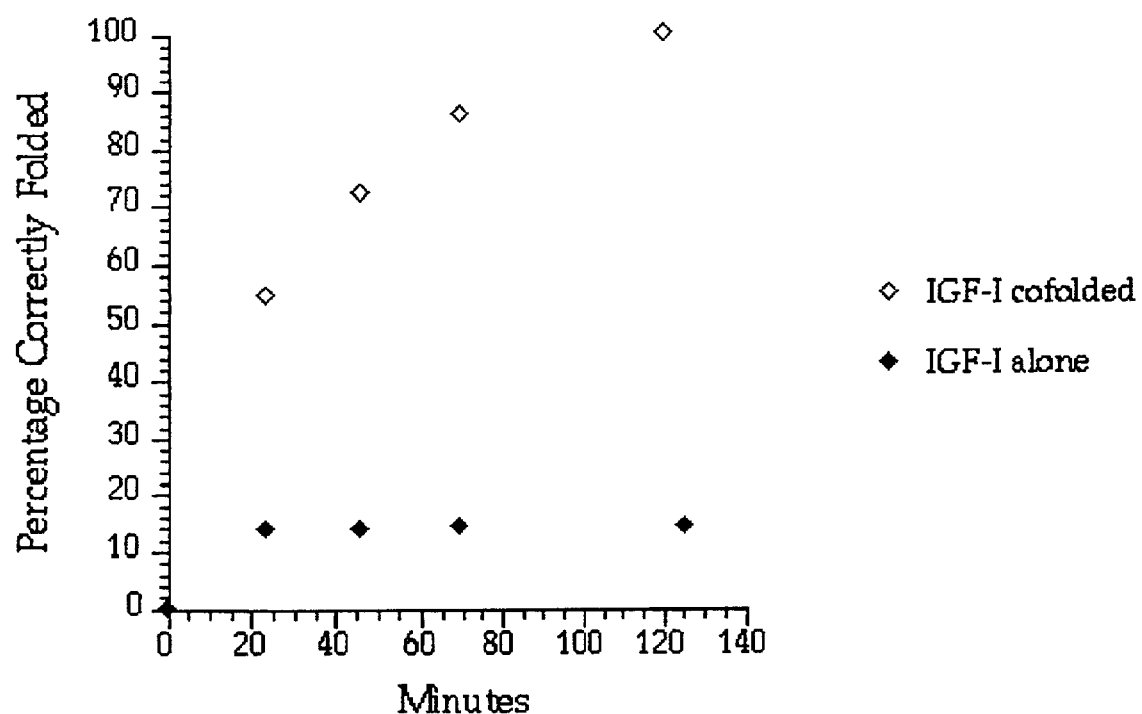
FIG. 9 and FIG. 10 show the results of cofolding IGF-I and IGFBP-3. Filled diamonds represent refolding of IGF-I or IGFBP-3 alone, respectively, while open diamonds represent the results from cofolding.

Proteins expressed at high levels in recombinant expression systems frequently exhibit low or undetectable biological activity, due to improper folding and incorrect disulfide bond formation. The present invention provides a novel method for rapidly refolding recombinantly produced IGF-I and IGFBP-3 at extremely high efficiency, yielding native IGF-I and IGFBP-3. In a surprising result, the inventors found that oxidation of a mixture of denatured and reduced IGF-I and IGFBP-3, i.e., cofolding, [combination of unfolded or improperly folded IGF-I with unfolded or improperly folded IGFBP-3 under denaturing and reducing conditions, followed by oxidation,] resulted in a synergistic increase in the refolding efficiency for both proteins, yielding nearly 100% native IGF-I and a very high percentage of native IGFBP-3. The inventors also unexpectedly found that the kinetics of refolding were substantially altered, especially with respect to the folding of IGFBP-3, resulting in a considerable reduction in the time required for refolding. These results were particularly surprising because it is known that the disulfide isomerase activity (an enzymatic activity which involves the breaking and reforming of disulfide bonds and which can assist in protein refolding) of IGF-I is inhibited by the addition of equimolar amounts of IGFBP-3 (Koedam and Leo van den Brande, supra).

The invention also provides for efficient methods for the production of purified native IGF, native IGFBP-3 and native IGF/IGFBP-3 complex from recombinant expression systems. Cofolding of IGF-I and IGFBP-3 according to the instant invention results in the formation of native IGF-I/IGFBP-3 complexes. These complexes can be easily isolated from any improperly folded protein in the folding reaction using simple methods well known to those in the art. If desired, IGF-I and IGFBP-3 can each be easily further isolated and purified by methods well known to those in the art Definitions "Insulin-like growth factor" or "IGF" comprises a family of factors, including, but not limited to, IGF-I and IGF-II. IGF is a polypeptide with a molecular weight of about 7.5 Kd. IGF includes naturally occurring IGF-I or IGF-II, analogs or variants thereof, and fusions between IGF-I or IGF-II and other amino acid sequences. IGF may be obtained from natural sources or prepared by recombinant means.

"Insulin-like growth factor binding protein-3" or "IGFBP-3" as used herein is a member of the family of insulin-like growth factor binding proteins which comprises, but is not limited to, IGFBP-1, IGFBP-2, IGFBP-3, IGFBP-4, IGFBP-5, and IGFBP-6. IGFBP-3 may be obtained from natural sources or prepared by recombinant means. IGFBP-3 forms a complex with IGF and a third molecule known as ALS.

"Native IGF-I," as used herein, is defined as IGF-I, including naturally occurring IGF-I, analogs, and variants thereof, which is properly folded and contains only correct disulfide bonds. Correct disulfide bonds are formed between amino acid residues C6–C48, C47–52, and C18–C61, or the homologs of those amino acid residues in analogs and variants of IGF-I. Native IGF-I is biologically active.

"Insoluble IGF-I" refers to precipitated or aggregated IGF-I that is contained within host cells, or is otherwise host cell associated, and assumes a biologically inactive conformation with incorrect or unformed disulfide bonds. Insoluble IGF-I may be contained in inclusion bodies or retractile bodies, i.e., may or may not be visible under a phase contrast microscope.

"Improperly folded IGF-I" refers to IGF-I which is in a biologically inactive conformation with incorrect or unformed disulfide bonds. Improperly folded IGF-I may be, but need not be, insoluble.

"Insoluble IGFBP-3" refers to precipitated or aggregated IGFBP-3 that is contained within host cells, or is otherwise host cell associated, and assumes a biologically inactive conformation with incorrect or unformed disulfide bonds. The insoluble IGFBP-3 may be contained in inclusion bodies or refractile bodies, i.e., may or may not be visible under a phase contrast microscope.

"Improperly folded IGFBP-3" refers to IGFBP-3 which is in a biologically inactive conformation with incorrect or unformed disulfide bonds. Improperly folded IGFBP-3 may be, but need not be, insoluble.

"Native IGFBP-3," as used herein, is defined as IGFBP-3, including naturally occurring IGFBP-3, analogs, and variants thereof, which is properly folded and contains only correct disulfide bonds. Native IGFBP-3 is biologically active.

"Native IGF-I/IGFBP-3 complex," as used herein, is defined as a non-covalently bound complex of native IGF-I and native IGFBP-3.

"Reducing agent," as used herein, is defined as any compound or material which maintains sulfhydryl groups in the reduced state and reduces intra- or intermolecular disulfide bonds. Acceptable reducing agents include, but are not limited to, dithiothreitol (DTT), 2-mercaptoethanol, dithioerythritol, cysteine, cysteamine (2-aminoethanethiol), and reduced glutathione.

"Oxidizing agent," as used herein, is defined as any compound or material which is capable of removing an electron from a compound being oxidized. Acceptable oxidizing agents include, but are not limited to, oxidized glutathione, cystine, cystamine, oxidized dithiothreitol, oxidized erythreitol, and oxygen.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Acceptable denaturing agents or denaturants may be chaotropes, detergents, organic, water miscible solvents, phospholipids, or a combination of two or more such agents. Acceptable chaotropes include, but are not limited to, urea, guanidine, and sodium thiocyanate. Useful detergents may include, but are not limited to, strong detergents such as sodium dodecyl sulfate, or polyoxyethylene ethers (e.g., Tween or Triton detergents), mild nonionic detergents (e.g., digitonin), mild cationic detergents such as N-[2,3-(Dioleyoxy)-propyl]-N,N,N-trimethylammonium, mild ionic detergents (e.g., sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl) dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process or method which is designed to transform polypeptide from its improperly folded or unfolded state to its native, properly folded conformation.

"Cofolding," as used herein, refers specifically to refolding processes, reactions, or methods which employ at least two polypeptides which interact with each other and result in the transformation of unfolded or improperly folded polypeptides to native, properly folded polypeptides.

DESCRIPTION OF THE PREFERRED EMBODIMENTS

The instant invention resides in the cofolding of IGF-I and IGFBP-3, resulting in rapid, highly efficient refolding of the two proteins, yielding native IGF-I and IGFBP-3, and further includes simplified methods for purification of native IGF-I, IGFBP-3, and IGF-I/IGFBP-3 complex. The invention may be carried out as follows:

a) IGF-I and IGFBP-3 are combined in a molar ratio of about 1:3 to 3:1, then denatured and reduced with denaturing and reducing agents, or alternatively, IGF-I and IGFBP-3 are denatured and reduced individually, then combined in a molar ratio of about 1:3 to 3:1 to form IGF-I/IGFBP-3 complex;

b) An oxidizing agent is then added to the IGF-I/IGFBP-3 mixture of step (a);

c) Optionally, IGF-I/IGFBP-3 complex may be purified from the IGF-I/IGFBP-3 cofolding mixture; and d) Optionally, IGF-I and IGFBP-3 may be individually purified from the complex.

IGF-I and IGFBP-3 for cofolding in accordance with the present invention may be produced in a variety of high expression systems, utilizing a variety of host cells, including, but not limited to, bacteria, yeast, insect and mammalian cell lines. Preferably, IGF-I and IGFBP-3 are produced in bacterial host cells. More preferably, IGF-I and IGFBP-3 are produced in E. coli host cells, including, but not limited to E. coli strain W3110DE3.

Host cells are transformed with expression vectors containing DNA coding for IGF-I or IGFBP-3. Host cells may be transformed by a variety of techniques well known to the art, such as, but not limited to, $CaCl_2$ for bacterial or yeast host cells, $CaPO_4$ for insect or mammalian host cells, or electroporation may be used for any host cell type. Methods for transformation of host cells may be found in Sambrook et al. (1989) MOLECULAR CLONING: A LABORATORY MANUAL (Cold Spring Harbor Laboratory Press, Cold Spring Harbor) and Ausubel (1987) CURRENT PROTOCOLS IN MOLECULAR BIOLOGY, (John Wiley & Sons, New York)

Expression vectors containing DNA coding for IGF-I or IGFBP-3 may be constructed by standard methods well known to the art. DNA coding for IGF-I or IGFBP-3 may be obtained from natural sources, such as genomic or cDNA libraries, or may be chemically synthesized. Further, variants of IGF-I or IGFBP-3 may be produced by a variety of methods well known to the art, including site-directed mutagenesis. Methods for the production of variants may be found in Sambrook, supra and Ausubel, supra.

Transformed microbial host strains are cultured in liquid medium containing assimilatable sources of carbon, nitrogen, and inorganic salts, using methods that are well known to the art. Transformed insect or mammalian cells are cultured in liquid medium containing assimilatable sources of carbon, nitrogen, and inorganic salts and, optionally, containing vitamins, amino acids, growth factors, and other proteinaceous culture supplements known to the art. Liquid media for culture of host cells may optionally contain antibiotics or antifungals to prevent the growth of undesirable microorganisms and/or compounds including, but not limited to, antibiotics to select for host cells containing the expression vector.

IGF-I and IGFBP-3 may be purified from host cells by a variety of methods known to the art. Normally, IGF-I or IGFBP-3 produced in bacterial host cells is poorly soluble or insoluble (in the form of inclusion bodies). In the case of insoluble protein, the protein may be collected from host cell lysates by centrifugation. In the case of poorly soluble protein, compounds including, but not limited to, polyethylene imine (PEI) may be added to induce the precipitation of partially soluble protein. The precipitated protein may then be conveniently collected by centrifugation.

Insoluble or precipitated IGF-I or IGFBP-3 may then be solubilized using any of a number of agents known to the art. Preferably, IGF-I or IGFBP-3 is solubilized with urea or guanidine hydrochloride.

When IGF-I or IGFBP-3 is produced as a fusion protein, the fusion sequence may optionally be removed. Removal of a fusion sequence may be accomplished by enzymatic or chemical cleavage, preferably by enzymatic cleavage. Enzymatic removal of fusion sequences may be accomplished using methods well known to those in the art. The choice of enzyme for removal of the fusion sequence will be determined by the identity of the fusion, and the reaction conditions will be specified by the choice of enzyme as will be apparent to one skilled in the art. The cleaved IGF-I or IGFBP-3 may further be purified from the cleaved fusion sequence by well known methods. Such methods will be determined by the identity and properties of the fusion sequence as will be apparent to one skilled in the art. Methods for purification may include, but are not limited to, size-exclusion chromatography, hydrophobic interaction chromatography, ion-exchange chromatography, or dialysis.

IGF-I or IGFBP-3 is preferably further purified to remove DNA from the protein solution. DNA may be removed by any of several methods known to the art, such as precipitation or ion exchange chromatography, but is preferably removed by precipitation with protamine sulfate. IGF-I or IGFBP-3 may be separated from the precipitated DNA using methods including centrifugation or filtration.

IGF-I or IGFBP-3 for cofolding in accordance with the present invention may be used directly following the removal of DNA, or may be further purified and/or concentrated using methods well known to the art. Cofolding of relatively impure (crude) IGF-I and IGFBP-3 has the advantage of increasing yields and simplifying purification of native IGF-I/IGFBP-3 complex. Purification of cofolded complex requires only one purification protocol (as opposed to two, when the two polypeptides are purified separately before cofolding), and allows the purification protocol to exploit the properties of native IGF-I/IGFBP-3 complex.

If desired, IGF-I and IGFBP-3 may be further purified. Purification of IGF-I and IGFBP-3 may be accomplished using a variety of techniques well known to the art, including hydrophobic interaction chromatography, size exclusion chromatography, ion exchange chromatography, reverse-phase high performance liquid chromatography, affinity chromatography, and the like. Additional purification may also include a step of drying or precipitation of the purified protein. When IGF-I and IGFBP-3 are dried or precipitated, the proteins may be combined before redissolving in denaturant, or may be redissolved individually and combined for cofolding.

Denaturation of IGF-I and IGFBP-3 may be accomplished using a variety of denaturing agents, including, but not limited to, urea or guanidine. Preferably, the denaturant is urea. Denaturation may be accomplished in a one step process, wherein IGF-I and IGFBP-3 are denatured with a solution of denaturant which is the concentration used for cofolding, or in a two step process in which IGF-I and IGFBP-3 are denatured with a high concentration of denaturant, followed by dilution, resulting in a solution containing a concentration of denaturant useful in the cofolding process. In the one step denaturation process, the concentration of denaturant, where the denaturant is urea, is preferably about 1 to 2 molar. In the two step denaturation process, the concentration of denaturant, where the denaturant is urea, is preferably about 5 to 7 molar, which is preferably diluted to about 1 to 2 molar for the cofolding process.

Reduction of IGF-I and IGFBP-3 may be accomplished at the same time as denaturation or, optionally, may be accomplished following denaturation. Reduction of IGF-I and IGFBP-3 may be accomplished with a variety of agents, including, but not limited to, dithiothreitol (DTT), 2-mercaptoethanol, cysteine, cysteamine (2-aminoethanethiol), or reduced glutathione. Preferably the reducing agent is DTT. As discussed for denaturation, reduction of IGF-I and IGFBP-3 can be a one or two step process wherein the polypeptides are reduced using a concentration of reductant useful in the cofolding process or wherein the polypeptides are reduced with a high concentration of reductant, followed by dilution to a concentration useful in the cofolding process. Where the reductant is DTT, the high concentration of reductant is preferably about 30 to 50 millimolar (mM), and the concentration useful for cofolding is preferably about 5 to 15 mM.

The solution of denatured and reduced IGF-I and IGFBP-3 is then oxidized to form disulfide bonds. Acceptable oxidizing agents include, but are not limited to, glutathione, cystine, and cystamine. Preferably the oxidizing agent is cystamine.

The cofolding reaction may be allowed to continue indefinitely. However, the inventors have found that cofolding of IGF-I and IGFBP-3 substantially speeds the kinetics of refolding. Accordingly, the reaction may be allowed to continue for considerably shorter periods, as short as 1 to 2 hours. Preferably the cofolding reaction is continued for up to 4 hours, more preferably the cofolding reaction is continued for about 1 to 3 hours.

Following the completion of the cofolding reaction, native IGF-I/IGFBP-3 complex may be purified. Native IGF-I/IGFBP-3 complex may be purified by a variety of methods, including, but not limited to, size exclusion, ion exchange chromatography, and hydrophobic interaction chromatography. Preferably, native IGF-I/IGFBP-3 complex is purified by cation exchange chromatography using a sulfopropyl-derivatized column chromatography matrix, (e.g., SP-Sephadex, Pharmacia, Uppsala, Sweden). Optionally, native IGF-I and IGFBP-3 may be further purified from the complex using a variety of methods known to the art. Preferably IGF-I and IGFBP-3 are purified from the complex by dissociation of the complex, preferably under acidic conditions, followed by size exclusion chromatography. Purified complex or IGF-I or IGFBP-3 may be exchanged into different buffers and/or concentrated by any of a variety of methods known to the art.

The following examples are intended to illustrate the present invention. The examples are not intended to limit the scope of the present invention in any way.

EXAMPLES

Example 1

Expression vectors containing IGF-I and IGFBP-3 sequences for use in the production of IGF-I and IGFBP-3.

The expression constructs used to produce IGF-I and IGFBP-3 are similar to pJU1002 and pJU1003 (Squires et al. (1988) *J. Biol. Chem.* 263: 16297–16302) except that the genes inserted downstream of the translational coupler are ubiquitin-IGF (pER10088) and IGFBP-3 (pDJ12833). In addition, pER10088 and pDJ12833 differ from pJU1003 in that they do not contain the synthetic 16 bp adaptor sequence at the 5' end of the tet gene in that plasmid; but they do contain DNA insertions at the unique PvuII site in the pBR322-derived backbone: pER10088 contains a linker 5'. . . CCTCGAGG . . . 3' at that location; pDJ12833 contains a 385 bp fragment carrying the par locus of pSC101 (Meacock and Cohen (1980) *Cell* 20: 529–542).

pER10088 contains an open reading frame (ORF) comprising (in order, 5' to 3') an ATG triplet (initiation), the 76 codons of yeast ubiquitin, 70 synthetic codons of mature human insulin growth factor I, and a termination codon.

PDJ12833 contains an ORF comprising an ATG triplet followed by the 264 codons of mature human IGFBP-3. The amino-terminal 95 codons are synthetic; the remainder were derived from the natural cDNA for this gene.

In each case, the ORF is positioned relative to the translational coupler exactly as described by Squires et al. (1988) for fibroblast growth factor.

Example 2

Recombinant production of IGF-I.

IGF-I may be produced using expression vector constructs such as those described in Example 1. An expression construct for production of an IGF-I fusion protein (PER10088) was introduced into *E. coli* strain W3110DE3 using calcium chloride transfection (Sambrook, supra).

W3110DE3/PER10088 was cultured in a 100 liter liquid culture at 37° C. until the culture reached an optical density at 600 nm ($OD_{600}$) of at least about 25. Expression of IGF-I was induced by the addition of isopropylthiogalactoside (IPTG) to a concentration of 0.4 mM. The induced bacteria were further cultured, then collected by centrifugation. The pelleted cells were resuspended in sodium acetate buffer (50 mM, pH 5.5) with ethylene diamine tetraacetate (EDTA). Bacteria were lysed with a Microfluidizer® (model M-210-EH, Microfluidics Corp.). Because not all of the IGF-I fusion protein produced in these host cells is insoluble, polyethyleneimine (PEI) was added to a concentration of 0.1% to precipitate soluble and partially soluble IGF-I fusion protein.

Insoluble and precipitated IGF-I fusion protein was collected by centrifugation, then washed once with 2M urea, 50 mM potassium phosphate, 2 mM DTT, pH 5.8–5.9, and recollected by centrifugation. The IGF-I pellet was then solubilized with 6M urea, 20 mM Tris, 30 mM DTT, 1 mM EDTA, pH 8.0. DNA was precipitated from the solution by the addition of protamine sulfate to a final concentration of 0.14%. Precipitated DNA was removed by centrifugation and the IGF-I fusion protein-containing supernatant was further purified by ion exchange chromatography on Q-Sepharose. IGF-I fusion protein was digested with ubiquitin hydrolase (which was obtained from *E. coli* by expression of pER1011, an expression vector encoding yeast ubiquitin hydrolase (the sequence encoding yeast ubiquitin hydrolase is shown in FIG. 8), followed by purification according to Liu et al. ((1989) *J. Biol. Chem.* 264:20331–20338) (PER1011 is analogous to PJU1002 except for the presence of the 5'... CCTCGAGG ... 3' linker at the PvuII site), yielding mature IGF-I.

IGF-I was then denatured and refolded in 2M urea, 10 millimolar DTT and 20% ethanol in the presence of 10 millimolar cystamine. IGF-1 was further purified by cation exchange chromatography on SP-Sepharose and reverse-phase high performance liquid chromatography (RP-HPLC) on a $C_{18}$ column (Vydac).

Example 3

Recombinant production of IGFBP-3.

IGFBP-3 may be produced using expression vector constructs such as those shown in Example 1. An expression construct for production of an IGFBP-3 PDJ12833 was introduced into *E. coli* strain W3110DE3 and clones were isolated, using methods well known to those in the art (such as those described in Sambrook, supra and Ausubel, supra).

Clone W3110DE3/PDJ12833 was cultured in a 100 L liquid culture at 37° C. until the culture reached an optical density at 600 nm ($OD_{600}$) of 25. Expression of IGFBP-3 was induced by the addition of isopropylthiogalactoside (IPTG) to a concentration of 0.4 mm. The induced bacteria were further cultured, then collected by centrifugation. The pelleted cells were resuspended in sodium acetate buffer (50 mM, pH 5.5) with ethylene diamine tetraacetate (EDTA). Bacteria were lysed with a Microfluidizer® (model M-210-EH, Microfluidics Corp.).

Insoluble IGFBP-3 was collected by centrifugation, then washed once with 2M urea, 50 mM potassium phosphate, 2 mM DTT, pH 5.8–5.9, and recollected by centrifugation. The IGFBP-3 pellet was then solubilized with 6M guanidinium Hcl, 100 mM Tris, 25 mM DTT, 5 mM EDTA, pH 8.0, then the IGFBP-3-containing solution was diluted with 1 volume of 100 mM Tris, 5 mM EDTA, pH 8. DNA was precipitated from the solution by the addition of protamine sulfate to a final concentration of 0.14%. Precipitated DNA was removed by centrifugation and the IGFBP-3-containing supernatant was further diluted with 50 mM Tris, pH 10.6. IGFBP-3 was refolded overnight following the addition of cystamine to a final concentration of 6 mM.

The IGFBP-3 solution was concentrated by ultrafiltration, then solvent exchanged by diafiltration against 2M urea, 20 mM Tris, pH 7. IGFBP-3 was purified by ion exchange chromatography on Q-Sepharose followed by SP-Sepharose. The IGFBP-3 was further purified by RP-HPLC using a $C_{18}$ column (Vydac).

Example 4

Cofolding of IGF-I and IGFBP-3.

Recombinantly produced IGF-I and IGFBP-3 were mixed in an equimolar ratio, then dried by lyophilization. The dried protein mixture was dissolved in denaturing/reducing buffer (80 mM Tris, pH 8.3, 1.5M urea, 1 mM EDTA, 10 mM DTT) to a final protein concentration of 1 mg/ml. Cystamine hydrochloride was added to a final concentration of 10 mM cystamine. Controls were IGF-I refolded alone and IGFBP-3 refolded alone. Cofolding and refolding reactions were incubated at 5° C. Samples were taken immediately before (0 hour), and at 1, 2, 3, and 4 hours after the addition of cystamine and analyzed RP-HPLC. RP-HPLC analysis of 0 hour time points indicated that both the IGF-I and the IGFBP-3 were fully reduced. RP-HPLC was performed with a Waters 626-1 HPLC instrument on a Poros R2/H column (4.6 mm diameter, 100 mm length) using a linear gradient of acetonitrile (with 0.1.% trifluoracetic acid) running from 13.5% to 54% acetonitrile.

IGF-I and IGFBP-3 refolded alone gave poor yields of native protein. IGF-I refolded alone gave a yield of only 13% and IGFBP-3 refolded alone yielded 45.1% native protein. In contrast, when cofolded, virtually all (99.6%) of the IGF-I and most of the IGFBP-3 (83%) were correctly folded. These results indicate that cofolding of IGF-I and IGFBP-3 results in a synergistic increase in yields of native IGF-I and IGFBP-3.

Figure 10:
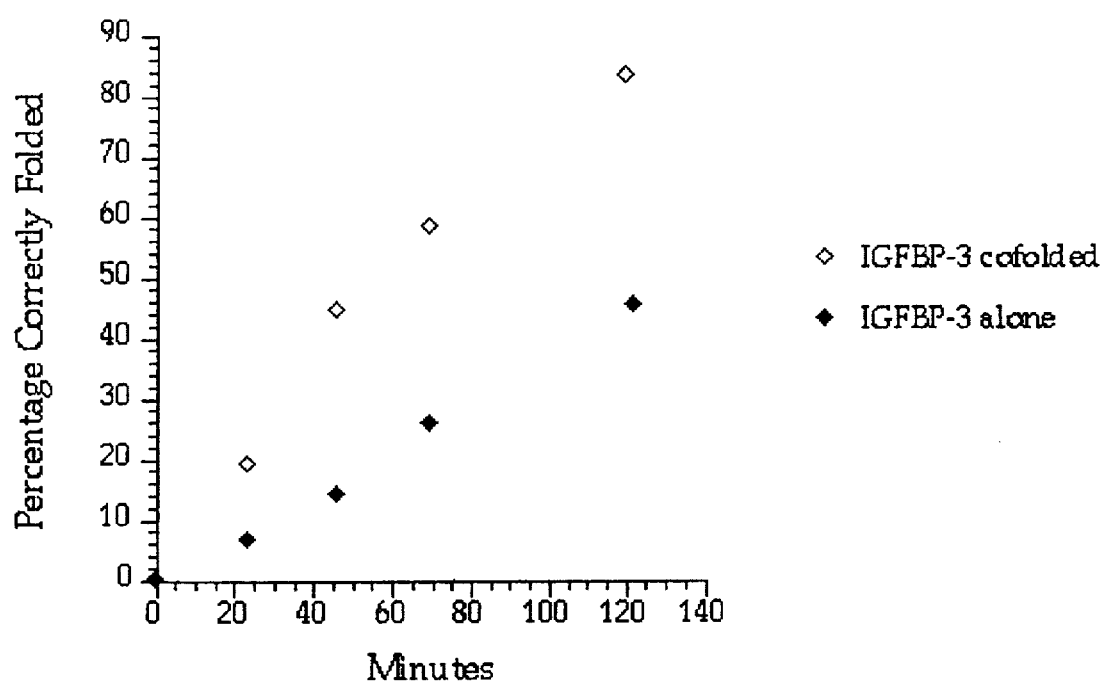

Further analysis of the cofolding reaction indicated that, in addition to increasing yields of native proteins, cofolding also alters the kinetics of refolding. FIGS. 9 and 10 show the time courses of refolding of IGF-I and IGFBP-3 either alone or in a cofolding reaction. The cofolding process increases the initial rate of refolding and the maximum rate of refolding as well as the total yield of refolding.

Example 5

Assay for bioactivity of cofolded IGF-I and IGFBP-3

This example shows that IGF-I, IGFBP-3, and IGF-I/IGFBP-3 complex refolded according to the present invention have biological activity.

Human osteosarcoma MG63 cells ($5 \times 10^5$ cells) are plated in a T-175 flask and cultured in cell culture medium (RPMI media supplemented with 10% fetal bovine serum, 50 units/ml penicillin, 50 µg/ml streptomycin, non-essential amino acids and 2 mM L-glutamine). The flask is incubated at 37° C. in a humidified 5% $CO_2$/95% air atmosphere for a 2–3 days. Before the culture of cells become confluent, the cells are detached from the flask by incubating the cells in trypsin/EDTA solution. Cell culture medium (6 ml) is added to stop the trypsin and the cells are transferred into a centrifuge tube. The cells are centrifuged at 800 xg for 5–10 minutes and resuspended in 10 ml of an assay medium (RPMI medium supplemented with 50 units/ml penicillin, 50 µg/ml streptomycin, non-essential amino acids, 2 mM L-glutamine, 2.5 µg/ml bovine fibronectin, 5 µg/ml human transferring, 75 µg/ml ovalbumin, and 3 µM dexamethasone).

IGF-I reference standard and cofolded IGF-I and IGFBP-3 samples are diluted serially with the assay medium in 96-well plates. IGF-I/IGFBP-3 complex, IGF-I, and IGFBP-3 refolded by the cofolding method are each tested. Each well contains 50 µl of the standard or test sample. The concentration range of the IGF-I reference standard is 0.244–500 ng/ml.

The MG63 human osteosarcoma cells that have been prepared in the assay medium are plated at 5000 cells/well, in volumes of 50 µl/well. The total volume in each well is 100 µl. The plates are incubated in a humidified 5% $CO_2$/95% air atmosphere for 4 days at 37° C.

At the end of the incubation period, cell growth is assayed by measuring acid phosphatase activity, which is proportional to the number of osteosarcoma cells. The plates are removed from the incubator and the culture medium is aspirated out of the wells. Each well is rinsed with 200 µl of phosphate-buffered saline. One hundred µl of 10 mM p-nitrophenyl phosphate, 100 mM sodium acetate, 1% Triton X-100, pH 5.5 is added to each well and the plate is incubated at 37° C. for 2 hours. The hydrolysis of p-nitrophenyl phosphate by acid phosphatases is stopped by adding to each well 10 µl of 1.0N sodium hydroxide. The plates are incubated at room temperature for a minimum of 10 minutes. Absorbance at 405 nm is measured, while referencing the absorbance at 490 nm.

Background absorbance is subtracted from the absorbance of each well. The averaged absorbance is plotted as a function of the concentration of IGF-I. $ED_{50}$, the concentration of IGF-I where the absorbance value is half of the maximum absorbance, is calculated for each sample and the reference standard from the dose-response plots. Activity of each sample is expressed as a ratio of the $ED_{50}$'s of IGF-I reference standard and the sample.

The present invention has been detailed both by direct description and by example. Equivalents and modifications of the present invention will be apparent to those skilled in the art, and are encompassed within the scope of the invention.

---

We claim:

1. A method for producing a complex of native insulin-like growth factor I (IGF-I) and insulin-like growth factor binding protein 3 (IGFBP-3), comprising:
   denaturing a mixture of naturally occurring IGF-I and IGFBP-3, wherein said mixture of IGF-I and IGFBP-3 is at a molar ratio of about 1:3 to 3:1, thereby forming a solution of denatured IGF-I and IGFBP-3;
   reducing said mixture of IGF-I and IGFBP-3, thereby forming a solution of reduced, denatured IGF-I and IGFBP-3;
   adding an oxidizing agent to said mixture of IGF-I and IGFBP-3; and
   forming a complex of native IGF-I and IGFBP-3.

2. The method of claim 1, further comprising isolating said complex of native IGF-I and IGFBP-3 from said mixture of IGF-I and IGFBP-3.

3. The method of claim 1, further comprising isolating native IGF-I from said complex of native IGF-I and IGFBP-3.

4. The method of claim 1, further comprising isolating native IGFBP-3 from said complex of native IGF-I and IGFBP-3.

5. The method of claim 1 further comprising the step of diluting said mixture of denatured, reduced IGF-I and IGFBP-3 before adding said oxidizing agent.

6. The method of claim 1 wherein said mixture of IGF-I and IGFBP-3 polypeptides is at a molar ratio of about 1.5:1 to 1:1.5.

7. The method of claim 1, wherein said mixture of IGF-I and IGFBP-3 is denatured with urea or guanidine, said mixture of IGF-I and IGFBP-3 is reduced with dithiothreitol, 2-mercaptoethanol, dithioerythritol, cysteine, cysteamine, or reduced glutathione, and said oxidizing agent is cystine, cystamine, oxygen, oxidized dithiothreitol, oxidized dithioerythritol, or oxidized glutathione.

8. The method of claim 1, wherein said mixture of IGF-I and IGFBP-3 is denatured with urea at a concentration of about 1–2 molar, said mixture of IGF-I and IGFBP-3 is reduced with dithiothreitol at a concentration of about 5 to 15 millimolar, and said oxidizing agent is cystamine at a concentration of about 5 to 15 millimolar.

9. The method of claim 1 wherein said IGFBP-3 is naturally occurring IGFBP-3.

10. A method for producing a complex of native insulin-like growth factor I (IGF-I) and insulin-like growth factor binding protein 3 (IGFBP-3), comprising:

purifying naturally-occurring IGF-I and purifying IGFBP-3;

denaturing a mixture of said naturally-occurring IGF-I and IGFBP-3;

reducing said mixture of IGF-I and IGFBP-3, thereby forming a solution of reduced, denatured IGF-I and IGFBP-3;

adding an oxidizing agent to said mixture of IGF-I and IGFBP-3; and forming a complex of native IGF-I and IGFBP-3.

11. A method for producing a complex of native insulin-like growth factor I (IGF-I) and insulin-like growth factor binding protein 3 (IGFBP-3), comprising:

denaturing naturally occurring IGF-I;

reducing said IGF-I, thereby producing denatured, reduced IGF-I;

denaturing IGFBP-3;

reducing said IGFBP-3, thereby producing denatured, reduced IGFBP-3;

mixing said denatured, reduced IGF-I with said denatured, reduced IGFBP-3, thereby forming a mixture of denatured, reduced IGF-I and IGFBP-3;

adding an oxidizing agent to said mixture of denatured, reduced IGF-I and IGFBP-3; and forming a complex of native IGF-I and IGFBP-3.

12. The method of claim 11 wherein said IGFBP-3 is naturally occurring IGFBP-3.

13. A method for producing a complex of native insulin-like growth factor I (IGF-I) and insulin-like growth factor binding protein 3 (IGFBP-3), comprising denaturing naturally occurring IGF-I, thereby forming denatured IGF-I;

denaturing IGFBP-3, thereby forming denatured IGFBP-3;

mixing said denatured IGF-I with said denatured IGFBP-3, thereby forming a mixture of denatured IGF-I and IGFBP-3;

reducing said mixture of denatured IGF-I and IGFBP-3, thereby forming a denatured, reduced mixture of IGF-I and IGFBP-3;

adding an oxidizing agent to said denatured, reduced mixture of IGF-I and IGFBP-3; and forming a complex of native IGF-I and IGFBP-3.

14. The method of claim 13 wherein said IGFBP-3 is naturally occurring IGFBP-3.

15. A method for producing a complex of native insulin-like growth factor I (IGF-I) and insulin-like growth factor binding protein 3 (IGFBP-3), consisting of:

denaturing a mixture of naturally occurring IGF-I and IGFBP-3, wherein said mixture is at a molar ratio of about 1:3 to 3:1;

reducing said mixture of IGF-I and IGFBP-3, thereby forming a solution of reduced, denatured IGF-I and IGFBP-3;

adding an oxidizing agent to said mixture of IGF-I and IGFBP-3; and forming a complex of native IGF-I and IGFBP-3.

16. The method of claim 15, said method further comprising purifying said IGF-I and IGFBP-3 prior to forming said mixture.

17. The method of claim 15, said method further comprising removing DNA from said mixture of IGF-I and IGFBP-3.

18. The method of claim 15 wherein said IGFBP-3 is naturally occurring IGFBP-3.

19. The method of claim 16, said method further comprising further purifying said denatured IGF-I.

20. The method of claim 16, said method further comprising further purifying said denatured IGFBP-3.

21. The method of claim 16, said method further comprising removing DNA from said denatured IGF-I.

22. The method of claim 16, said method further comprising removing DNA from said denatured IGFBP-3.

23. The method of claim 16, said method further comprising removing DNA from said mixture of denatured IGF-I and IGFBP-3.

24. The method of claim 16, said method further comprising removing DNA from said denatured, reduced mixture of IGF-I and IGFBP-3.

25. A method for producing a complex of native insulin-like growth factor I (IGF-I) and insulin-like growth factor binding protein 3 (IGFBP-3), consisting of:

denaturing naturally occurring IGF-I;

reducing said IGF-I, thereby producing denatured, reduced IGF-I;

denaturing IGFBP-3;

reducing said IGFBP-3, thereby producing denatured, reduced IGFBP-3;

mixing said denatured, reduced IGF-I with said denatured, reduced IGFBP-3, thereby forming a mixture of denatured, reduced IGF-I and IGFBP-3;

adding an oxidizing agent to said mixture of denatured, reduced IGF-I and IGFBP-3; and forming a complex of native IGF-I and IGFBP-3.

26. The method of claim 25, said method further comprising purifying said IGF-I and IGFBP-3 prior to forming said mixture.

27. The method of claim 25, said method further comprising removing DNA from said denatured IGF-I.

28. The method of claim 25, said method further comprising removing DNA from said denatured IGFBP-3.

29. The method of claim 25, said method further comprising removing DNA from said denatured, reduced IGF-I.

30. The method of claim 25, said method further comprising removing DNA from said denatured, reduced IGFBP-3.

31. The method of claim 25 wherein said IGFBP-3 is naturally occurring IGFBP-3.

32. A method for producing a complex of native insulin-like growth factor I (IGF-I) and insulin-like growth factor binding protein 3 (IGFBP-3), consisting of:

denaturing naturally occurring IGF-I, thereby forming denatured IGF-I;

denaturing IGFBP-3, thereby forming denatured IGFBP-3;

mixing said denatured IGF-I with said denatured IGFBP-3, thereby forming a mixture of denatured IGF-I and IGFBP-3;

reducing said mixture of denatured IGF-I and IGFBP-3, thereby forming a denatured, reduced mixture of IGF-I and IGFBP-3;

adding an oxidizing agent to said denatured, reduced mixture of IGF-I and IGFBP-3; and forming a complex of native IGF-I and IGFBP-3.

33. The method of claim 32, said method further comprising removing DNA from said mixture of denatured, reduced IGF-I and IGFBP-3.

34. The method of claim 32 wherein said IGFBP-3 is naturally occurring IGFBP-3.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 70 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Gly Pro Glu Thr Leu Cys Gly Ala Glu Leu Val Asp Ala Leu Gln Phe
 1               5                  10                  15
Val Cys Gly Asp Arg Gly Phe Tyr Phe Asn Lys Pro Thr Gly Tyr Gly
                20                  25                  30
Ser Ser Ser Arg Arg Ala Pro Gln Thr Gly Ile Val Asp Glu Cys Cys
            35                  40                  45
Phe Arg Ser Cys Asp Leu Arg Arg Leu Glu Met Tyr Cys Ala Pro Leu
        50                  55                  60
Lys Pro Ala Lys Ser Ala
 65              70
```

( 2 ) INFORMATION FOR SEQ ID NO:2:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear -continued ( x i ) SEQUENCE DESCRIPTION: SEQ ID NO:2:

```
ATGCAGATTT TCGTCAAGAC TTTGACCGGT AAAACCATAA CATTGGAAGT TGAATCTTCC        60
GATACCATCG ACAACGTTAA GTCGAAAATT CAAGACAAGG AAGGTATCCC TCCAGATCAA       120
CAAAGATTGA TCTTTGCCGG TAAGCAGCTA GAAGACGGTA GAACGCTGTC TGATTACAAC       180
ATTCAGAAGG AGTCCACCTT ACATCTTGTG CTAAGGCTCC GCGGTGGTGG TCCGGAAACC       240
CTGTGCGGTG CTGAACTGGT TGACGCTCTG CAGTTCGTTT GCGGTGACCG TGGTTTCTAC       300
TTCAACAAAC CGACCGGTTA CGGTTCCTCC TCCCGTCGTG CTCCGCAGAC CGGTATCGTT       360
GACGAATGCT GCTTCCGGTC CTGCGACCTG CGTCGTCTGG AAATGTACTG CGCTCCGCTG       420
AAACCGGCTA AATCCGCTTA A                                                 441
```

( 2 ) INFORMATION FOR SEQ ID NO:3:

( i ) SEQUENCE CHARACTERISTICS:
  ( A ) LENGTH: 264 amino acids
  ( B ) TYPE: amino acid
  ( C ) STRANDEDNESS: single
  ( D ) TOPOLOGY: linear ( x i ) SEQUENCE DESCRIPTION: SEQ ID NO:3:

```
Gly Ala Ser Ser Gly Gly Leu Gly Pro Val Val Arg Cys Glu Pro Cys
 1               5                  10                  15

Asp Ala Arg Ala Leu Ala Gln Cys Ala Pro Pro Pro Ala Val Cys Ala
             20                  25                  30

Glu Leu Val Arg Glu Pro Gly Cys Gly Cys Cys Leu Thr Cys Ala Leu
         35                  40                  45

Ser Glu Gly Gln Pro Cys Gly Ile Tyr Thr Glu Arg Cys Gly Ser Gly
     50                  55                  60

Leu Arg Cys Gln Pro Ser Pro Asp Glu Ala Arg Pro Leu Gln Ala Leu
 65                  70                  75                  80

Leu Asp Gly Arg Gly Leu Cys Val Asn Ala Ser Ala Val Ser Arg Leu
                 85                  90                  95

Arg Ala Tyr Leu Leu Pro Ala Pro Pro Ala Pro Gly Asn Ala Ser Glu
            100                 105                 110

Ser Glu Glu Asp Arg Ser Ala Gly Ser Val Glu Ser Pro Ser Val Ser
        115                 120                 125

Ser Thr His Arg Val Ser Asp Pro Lys Phe His Pro Leu His Ser Lys
    130                 135                 140

Ile Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
                165                 170                 175

Ser Lys Arg Glu Thr Glu Tyr Gly Pro Cys Arg Arg Glu Met Glu Asp
            180                 185                 190

Thr Leu Asn His Leu Lys Phe Leu Asn Val Leu Ser Pro Arg Gly Val
        195                 200                 205

His Ile Pro Asn Cys Asp Lys Lys Gly Phe Tyr Lys Lys Lys Gln Cys
    210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
            260
```

( 2 ) INFORMATION FOR SEQ ID NO:4:

( i ) SEQUENCE CHARACTERISTICS:
        ( A ) LENGTH: 264 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Gly Ala Ser Ser Ala Gly Leu Gly Pro Val Val Arg Cys Glu Pro Cys
 1               5                  10                  15
Asp Ala Arg Ala Leu Ala Gln Cys Ala Pro Pro Pro Ala Val Cys Ala
                20                  25                  30
Glu Leu Val Arg Glu Pro Gly Cys Gly Cys Cys Leu Thr Cys Ala Leu
            35                  40                  45
Ser Glu Gly Gln Pro Cys Gly Ile Tyr Thr Glu Arg Cys Gly Ser Gly
        50                  55                  60
Leu Arg Cys Gln Pro Ser Pro Asp Glu Ala Arg Pro Leu Gln Ala Leu
65                  70                  75                  80
Leu Asp Gly Arg Gly Leu Cys Val Asn Ala Ser Ala Val Ser Arg Leu
                85                  90                  95
Arg Ala Tyr Leu Leu Pro Ala Pro Ala Pro Gly Asn Ala Ser Glu
            100                 105                 110
Ser Glu Glu Asp Arg Ser Ala Gly Ser Val Glu Ser Pro Ser Val Ser
            115                 120                 125
Ser Thr His Arg Val Ser Asp Pro Lys Phe His Pro Leu His Ser Lys
        130                 135                 140
Ile Ile Ile Ile Lys Lys Gly His Ala Lys Asp Ser Gln Arg Tyr Lys
145                 150                 155                 160
Val Asp Tyr Glu Ser Gln Ser Thr Asp Thr Gln Asn Phe Ser Ser Glu
                165                 170                 175
Ser Lys Arg Glu Thr Glu Tyr Gly Pro Cys Arg Arg Glu Met Glu Asp
            180                 185                 190
Thr Leu Asn His Leu Lys Phe Leu Asn Val Leu Ser Pro Arg Gly Val
        195                 200                 205
His Ile Pro Asn Cys Asp Lys Lys Gly Phe Tyr Lys Lys Lys Gln Cys
    210                 215                 220
Arg Pro Ser Lys Gly Arg Lys Arg Gly Phe Cys Trp Cys Val Asp Lys
225                 230                 235                 240
Tyr Gly Gln Pro Leu Pro Gly Tyr Thr Thr Lys Gly Lys Glu Asp Val
                245                 250                 255
His Cys Tyr Ser Met Gln Ser Lys
                260
```

( 2 ) INFORMATION FOR SEQ ID NO:5:

( i ) SEQUENCE CHARACTERISTICS:
        ( A ) LENGTH: 798 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
ATGGGTGCAT CTTCTGCAGG TTTAGGTCCA GTTGTTCNTT GTGAACCATG TGATGCTCGT    60
GCTCTTGCTC AATGTGCTCC ACCACCAGCT GTTTGTGCTG AACTTGTTCG TGAACCGGGT   120
TGTGGTTGTT GTCTGACTTG TGCTCTTTCT GAAGGTCAAC CATGTGGTAT TTATACTGAA   180
CGTTGTGGTT CTGGTCTGCG TTGTCAACCA TCTCCAGATG AAGCTCGTCC TCTGCAGGCT   240
```

-continued

```
CTGCTGGACG GTCGTGGTCT GTGCGTTAAC GCTTCCGCTG TTTCCCGTCT GCGCGCCTAC    300
CTGCTGCCAG CGCCGCCAGC TCCAGGAAAT GCTAGTGAGT CGGAGGAAGA CCGCAGCGCC    360
GGCAGTGTGG AGAGCCCGTC CGTCTCCAGC ACGCACCGGG TGTCTGATCC CAAGTTCCAC    420
CCCCTCCATT CAAAGATAAT CATCATCAAG AAAGGGCATG CTAAAGACAG CCAGCGCTAC    480
AAAGTTGACT ACGAGTCTCA GAGCACAGAT ACCCAGAACT TCTCCTCCGA GTCCAAGCGG    540
GAGACAGAAT ATGGTCCCTG CCGTAGAGAA ATGGAAGACA CACTGAATCA CCTGAAGTTC    600
CTCAATGTGC TGAGTCCCAG GGGTGTACAC ATTCCCAACT GTGACAAGAA GGGATTTTAT    660
AAGAAAAAGC AGTGTCGCCC TTCCAAAGGC AGGAAGGGGG GCTTCTGCTG GTGTGTGGAT    720
AAGTATGGGC AGCCTCTCCC AGGCTACACC ACCAAGGGGA AGGAGGACGT GCACTGCTAC    780
AGCATGCAGA GCAAGTAG                                                  798
```

(2) INFORMATION FOR SEQ ID NO:6:

(i) SEQUENCE CHARACTERISTICS:
    (A) LENGTH: 811 base pairs
    (B) TYPE: nucleic acid
    (C) STRANDEDNESS: single
    (D) TOPOLOGY: linear (xi) SEQUENCE DESCRIPTION: SEQ ID NO:6:

```
GGTGCTTCTT CTGCTGGTCT TGGACCAGTT GTTCGTTGTG AACCATGTGA TGCACGAGCT     60
TTAGCTCAAT GTGCTCCACC ACCAGCTGTT TGTGCTGAAT TAGTTCGAGA ACCAGGTTGT    120
GGTTGTTGTT TAACTTGTGC TTTATCTGAA GGTCAACCAT GTGGTATTTA TACTGAACGT    180
TGCGGTAGTG GTTTGCGTTG TCAACCAAGC CCAGATGAAG CTAGGCCTTT ACAAGCATTA    240
TTAGATGGTC GAGGTCTGTG TGTTAATGCG TCCGCTGTTT CTCGATTGCG CGCTTATTTA    300
TTACCTGCCC CACCGGCACC GGGTAACGCC TCCGAAAGCG AAGAGGATCG TTCTGCGGGT    360
TCCGTTGAAT CTCCAAGTGT GAGTTCTACC CATCGAGTTA GCGACCCGAA ATTTCATCCG    420
TTGCACTCTA AAATCATTAT TATTAAAAAG GGTCACGCAA AGGATTCTCA ACGTTATAAG    480
GTGGATTATG AAAGCCAATC TACCGACACT CAAAATTTTA GTAGTGAAAG TAAACGTGAA    540
ACCGAGTACG GCCCGTGTCG ACGTGAGATG GAGGATACCT TAAACCATTT AAAATTTTTG    600
AACGTTTTAT CCCCGCGTGG CGTTCATATC CCGAATTGCG ATAAAAAAGG CTTCTACAAA    660
AAGAAACAAT GCCGTCCGAG TAAGGGTCGT AAACGAGGTT TTTGTTGGTG CGTTGACAAA    720
TACGGTCAAC CGTTGCCGGG TTATACTACT AAAGGCAAAG AAGATGTTCA TTGTTATTCT    780
ATGCAATCTA AATAATGCAT CTCGAGAATT C                                   811
```

(2) INFORMATION FOR SEQ ID NO:7:

(i) SEQUENCE CHARACTERISTICS:
    (A) LENGTH: 876 base pairs
    (B) TYPE: nucleic acid
    (C) STRANDEDNESS: single
    (D) TOPOLOGY: linear (xi) SEQUENCE DESCRIPTION: SEQ ID NO:7:

```
ATGCAGCGGG CGCGACCCAC GCTCTGGGCC GCTGCGCTGA CTCTGCTGGT GCTGCTCCGC     60
GGGCCGCCGG TGGCGCGGGC TGGCGCGAGC TCGGCGGGCT TGGGTCCCGT GGTGCGCTGC    120
GAGCCGTGCG ACGCGCGTGC ACTGGCCCAG TGCGCGCCTC CGCCCGCCGT GTGCGCGGAG    180
CTGGTGCGCG AGCCGGGCTG CGGCTGCTGC CTGACGTGCG CACTGAGCGA GGGCCAGCCG    240
TGCGGCATCT ACACCGAGCG CTGTGGCTCC GGCCTTCGCT GCCAGCCGTC GCCCGACGAG    300
```

```
GCGCGACCGC TGCAGGCGCT GCTGGACGGC CGCGGGCTCT GCGTCAACGC TAGTGCCGTC    360

AGCCGCCTGC GCGCCTACCT GCTGCCAGCG CCGCCAGCTC CAGGAAATGC TAGTGAGTCG    420

GAGGAAGACC GCAGCGCCGG CAGTGTGGAG AGCCCGTCCG TCTCCAGCAC GCACCGGGTG    480

TCTGATCCCA AGTTCCACCC CCTCCATTCA AAGATAATCA TCATCAAGAA AGGGCATGCT    540

AAAGACAGCC AGCGCTACAA AGTTGACTAC GAGTCTCAGA GCACAGATAC CCAGAACTTC    600

TCCTCCGAGT CCAAGCGGGA GACAGAATAT GGTCCCTGCC GTAGAGAAAT GGAAGACACA    660

CTGAATCACC TGAAGTTCCT CAATGTGCTG AGTCCCAGGG GTGTACACAT TCCCAACTGT    720

GACAAGAAGG GATTTTATAA GAAAAAGCAG TGTCGCCCTT CCAAAGGCAG GAAGCGGGGC    780

TTCTGCTGGT GTGTGGATAA GTATGGGCAG CCTCTCCCAG GCTACACCAC CAAGGGGAAG    840

GAGGACGTGC ACTGCTACAG CATGCAGAGC AAGTAG                              876
```

( 2 ) INFORMATION FOR SEQ ID NO:8:

( i ) SEQUENCE CHARACTERISTICS:
        ( A ) LENGTH: 711 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
ATGAGCGGAG AAAATCGTGC TGTGGTGCCG ATTGAATCAA ACCCTGAAGT TTTTACAAAT    60

TTTGCACATA AATTAGGTTT AAAAAATGAA TGGGCGTATT TCGATATCTA TAGCTTAACA    120

GAGCCAGAGT TACTAGCATT CTTACCAAGG CCAGTGAAGG CCATTGTGCT GCTATTTCCG    180

ATAAACGAGG ATAGAAAATC GAGTACCAGT CAACAAATTA CAAGTTCTTA TGATGTTATA    240

TGGTTTAAGC AATCAGTCAA AAATGCGTGC GGATTGTATG CAATTCTTCA TTCTTTGAGC    300

AATAACCAGT CATTGTTGGA GCCCGGCTCC GACTGGACA ATTTTTTAAA ATCTCAAAGT     360

GATACTTCAA GCTCGAAGAA TAGGTTTGAT GATGTTACTA CCGACCAATT CGTCTTGAAT    420

GTAATAAAAG AGAATGTACA AACATTTTCT ACTGGCCAGT CAGAAGCACC AGAAGCAACT    480

GCAGATACTA ATCTACACTA TATCACATAT GTGGAAGAGA ACGGAGGGAT ATTTGAACTG    540

GATGGAAGGA ATTTGAGCGG ACCCCTCTAT TTGGGAAAGA GTGACCCAAC TGCCACCGAT    600

TTGATTGAAC AGGAATTAGT TAGAGTGAGA GTCGCCTCAT ATATGGAAAA TGCAAATGAA    660

GAAGATGTAT TAAACTTTGC TATGCTAGGA TTGGGCCCTA ATTGGGAATA A            711
```